(12) United States Patent
Saito et al.

(10) Patent No.: US 7,501,358 B2
(45) Date of Patent: Mar. 10, 2009

(54) ADHESIVE PREPARATION

(75) Inventors: Junichi Saito, Ibaraki (JP); Akinori Hanatani, Ibaraki (JP); Hitoshi Akemi, Ibaraki (JP)

(73) Assignee: Nitto Denko Corporation, Osaka (JP)

( * ) Notice: Subject to any disclaimer, the term of this patent is extended or adjusted under 35 U.S.C. 154(b) by 0 days.

(21) Appl. No.: 11/402,004

(22) Filed: Apr. 12, 2006

(65) Prior Publication Data

US 2006/0234581 A1    Oct. 19, 2006

(30) Foreign Application Priority Data

Apr. 13, 2005    (JP)    ............................. 2005-116081

(51) Int. Cl.
*B32B 27/04*    (2006.01)
(52) U.S. Cl. .................... 442/151; 442/149; 428/32.79
(58) Field of Classification Search ................. 442/149, 442/151
See application file for complete search history.

(56) References Cited

U.S. PATENT DOCUMENTS

| | | | |
|---|---|---|---|
| 5,336,210 A | 8/1994 | Hidaka et al. | |
| 5,374,429 A | 12/1994 | Kinoshita et al. | |
| 5,650,165 A * | 7/1997 | Akemi et al. ................. | 424/448 |
| 6,914,169 B1 | 7/2005 | Oota et al. | |
| 2003/0138479 A1 | 7/2003 | Mizota et al. | |
| 2004/0156886 A1 | 8/2004 | Kose | |

FOREIGN PATENT DOCUMENTS

| | | |
|---|---|---|
| EP | 0 484 543 A1 | 5/1992 |
| EP | 0 531 938 B1 | 1/1997 |
| EP | 0 900 565 A1 | 3/1999 |
| EP | 0 435 199 B2 | 1/2000 |
| EP | 0 968 712 A1 | 1/2000 |
| EP | 1 287 824 A1 | 3/2003 |
| EP | 1 462 121 A1 | 9/2004 |
| JP | 5-238931 A | 9/1993 |
| JP | 6-35381 B2 | 5/1994 |
| JP | 7-25665 B2 | 3/1995 |
| JP | 2700835 B2 | 10/1997 |
| JP | 2886021 B2 | 2/1999 |
| JP | 3014188 B2 | 12/1999 |
| JP | 3081858 B2 | 6/2000 |
| JP | 2000-297032 A | 10/2000 |

(Continued)

*Primary Examiner*—Lynda Salvatore
(74) *Attorney, Agent, or Firm*—Wenderoth, Lind & Ponack, L.L.P.

(57) ABSTRACT

The present invention provides an adhesive preparation superior in adhesion property, which does not peel off or fall off easily and which can be adhered for a long time. An adhesive preparation 10 has a support 1 made of a cloth, and a pressure sensitive adhesive layer 3 formed on one surface of the support 1, which contains a pressure sensitive adhesive and a drug. The ratio (CW/AW) of a mass (CW) per unit area of the support 1 and a mass (AW) per unit area of the pressure sensitive adhesive layer 3 is 1.0-5.0, an adhesive layer-free surface of the support 1 has a static friction coefficient of 0.25-0.75, and a 20% modulus (AM) in one direction of the adhesive preparation 10 and a 20% modulus (EM) in the direction perpendicular to that direction are each 0.5-1.5 N/cm, and the ratio thereof (AM/EM) is 0.5-2.0.

3 Claims, 1 Drawing Sheet

FOREIGN PATENT DOCUMENTS

| | | |
|---|---|---|
| JP | 2001-328935 A | 11/2001 |
| JP | 2001-524623 A | 12/2001 |
| JP | 3499247 B2 | 12/2003 |
| WO | 99/27875 | 6/1999 |
| WO | 01/95889 A1 | 12/2001 |
| WO | 02/100384 A1 | 12/2002 |

* cited by examiner

ADHESIVE PREPARATION

TECHNICAL FIELD OF THE INVENTION

The present invention relates to an adhesive preparation superior in adhesion property, which does not peel off or fall off easily and which can be adhered for a long time.

BACKGROUND OF THE INVENTION

In recent years, adhesive preparations comprising a plastic thin layer film mainly made of polyethylene terephthalate and polypropylene as a support, and a pressure sensitive adhesive layer comprising an adhesive and a drug, which is formed on one side of the support, have been widely used. As an adhesive preparation, for example, a systemic or topical transdermally absorptive adhesive preparation, a flexible plaster containing an inflammatory analgesic and the like can be mentioned. However, in some of the transdermally absorptive adhesive preparations, a part of an adhesive may extrude from the periphery of a support due to cold flow, and the extruded adhesive may attach to and stain clothes during application, and an adhesive preparation may often peel off during putting on or taking off clothes. In addition, a glue may often remain on the skin along the periphery of an adhesive preparation during peeling off. On the other hand, since the friction of a surface free of an adhesive layer of the support of plaster is high, an adhesive preparation may be inconveniently peeled off and fall off during putting on/taking off clothes. It may happen, moreover, that a plaster has sufficient flexibility and stretchability in a certain direction but poor flexibility and stretchability in the direction perpendicular thereto, which in turn may result in foreign body sensation during adhesion, and peeling off or falling off of the plaster due to insufficient flexibility and stretchability of the bending part.

To improve such defects of conventional adhesive preparations, the following methods have been proposed. For example, as a method for preventing extrusion of a part of an adhesive from the periphery of a support due to cold flow, a method of limiting flowability by crosslinking a polymer constituting an adhesive with a reactive substance and the like (JP-B-2700835 and JP-B-3014188), a method of limiting flowability by the use of a support film having good affinity with an adhesive (JP-B-6-35381 and JP-B-7-25665), a method of suppressing flowability by physical disorder by laminating a cloth such as non-woven fabric and the like on a support film (JP-B-3081858 and JP-B-2886021) and the like have been proposed. According to the methods described in JP-B-2700835, JP-B-3014188, JP-B-6-35381, JP-B-7-25665, JP-B-3081858 and JP-B-2886021, the inconvenience of extrusion of a part of an adhesive from the periphery of a support due to cold flow can be almost resolved, but due to the use of a poorly stretchable member as a support, problems occur in that the followability to the movement of the skin is poor, foreign body sensation occurs considerably during adhesion, and application to a bending part is difficult, thus limiting the adhesion site.

As a method for improving the problem of sufficient flexibility and stretchability in a certain direction but poor flexibility and stretchability in the direction perpendicular thereto, there have been proposed a method of providing an adhesive preparation having a 50% modulus in one direction of 10-600 g/cm (JP-A-5-238931), a method of providing an adhesive preparation of a laminate having a stretchable support and an adhesive layer, wherein the load at 50% elongation in the long side direction and the short side direction is 0.98-14.71 N/5 cm (WO01/095889), a method of providing an adhesive preparation showing a strength in the longitudinal direction of 200 g-3 kg and a strength in the transverse direction of 100 g-600 g in a 30% modulus test under the measurement conditions of elongation strength of 200 mm/min, using a test piece obtained by cutting an adhesive sheet having a stretchable polyester woven fabric as a support into a 50 mm wide, 200 mm long piece (JP-B-3499247) and the like. However, according to the methods described in JP-A-5-238931 and WO01/095889, the adhesive preparation is elongated too much and is not suitable for prediction of foreign body sensation and comfortableness during actual adhesion, and the adhesive preparation described in JP-B-3499247 causes foreign body sensation depending on the adhesion state because the 30% moduli in the longitudinal direction and the transverse direction are different. In addition, as a method of reducing the friction of a support, there have been proposed a method of providing an adhesive preparation wherein a support has a static friction coefficient of 0.5-2.5 (WO02/100384) and the like. However, when the static friction coefficient of the support exceeds 0.75, the friction becomes too high and the adhesive preparation may peel off or sometimes fall off because of the friction with clothes.

SUMMARY OF THE INVENTION

The present invention has been made in view of such situation and aims at providing an adhesive preparation superior in adhesion property, which does not peel off or fall off easily and which can be adhered for a long time.

The present inventors have conducted intensive studies in an attempt to solve the above-mentioned problems and found that the above-mentioned problems can be solved when an adhesive preparation integrally comprising a support and a pressure sensitive adhesive layer satisfies a certain mass ratio per unit area of the support and the pressure sensitive adhesive layer, a certain static friction coefficient of an adhesive layer-free surface of the support, and certain levels of 20% modulus in given directions of the adhesive preparation and a certain proportion thereof, which resulted in the completion of the present invention.

Accordingly, the present invention provides the following.
(1) an adhesive preparation comprising a support made of a cloth, and a pressure sensitive adhesive layer formed on one surface of the support, which comprises a pressure sensitive adhesive and a drug, wherein
a ratio (CW/AW) of a mass (CW) per unit area of the above-mentioned support and a mass (AW) per unit area of the above-mentioned pressure sensitive adhesive layer is 1.0-5.0,
an adhesive layer-free surface of said support has a static friction coefficient of 0.25-0.75, and
a 20% modulus (AM) in one direction of the adhesive preparation and a 20% modulus (EM) in the direction perpendicular to said direction are each 0.5-1.5 N/cm, and the ratio thereof (AM/EM) is 0.5-2.0.
(2) The adhesive preparation of the above-mentioned (1), which has a shear adhesive force of 1.0-7.0 N/cm$^2$.
(3) The adhesive preparation of the above-mentioned (1) or (2), wherein the above-mentioned cloth is made of a synthetic fiber.
(4) The adhesive preparation of any of the above-mentioned (1) to (3), wherein the above-mentioned cloth is a knitted fabric.
(5) The adhesive preparation of any of the above-mentioned (1) to (4), wherein the above-mentioned cloth is made of polyethylene terephthalate.

(6) The adhesive preparation of any of the above-mentioned (1) to (5), wherein the above-mentioned pressure sensitive adhesive comprises an acrylic copolymer obtained by copolymerization of a monomer mixture comprising (meth)acrylic acid alkyl ester as a main component.

The adhesive preparation of the present invention seldom causes foreign body sensation or itchiness during adhesion, and provides comfortable feeling of adhesion. Due to low friction of the support, moreover, glue remainder during adhesion and peeling off is suppressed. In addition, since the adhesive preparation is rich in followability to the stretching of adhesion site during exercise and daily life, it does not peel off or fall off during putting on and taking off of clothes and during adhesion. Furthermore, since the adhesive preparation of the present invention does not fall off after 3 days' adhesion but can retain the aforementioned superior comfortable feeling of adhesion, it is applicable to the adhesion site for a long time.

DETAILED DESCRIPTION OF THE INVENTION

The present invention is explained in detail in the following by referring to a preferable embodiment. In the explanation of the Figures, the same reference symbol is assigned to the same element and duplicated explanations are omitted. In addition, for the convenience's sake, the size ratios in the Figures do not necessarily match those in the explanations.

Figure 1:
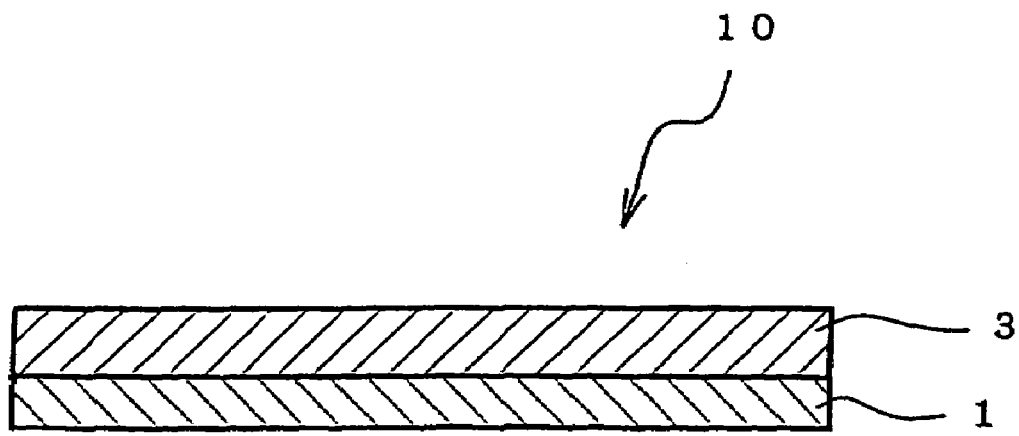
FIG. 1 is a sectional view showing one embodiment of the adhesive preparation of the present invention.
Figure 2:
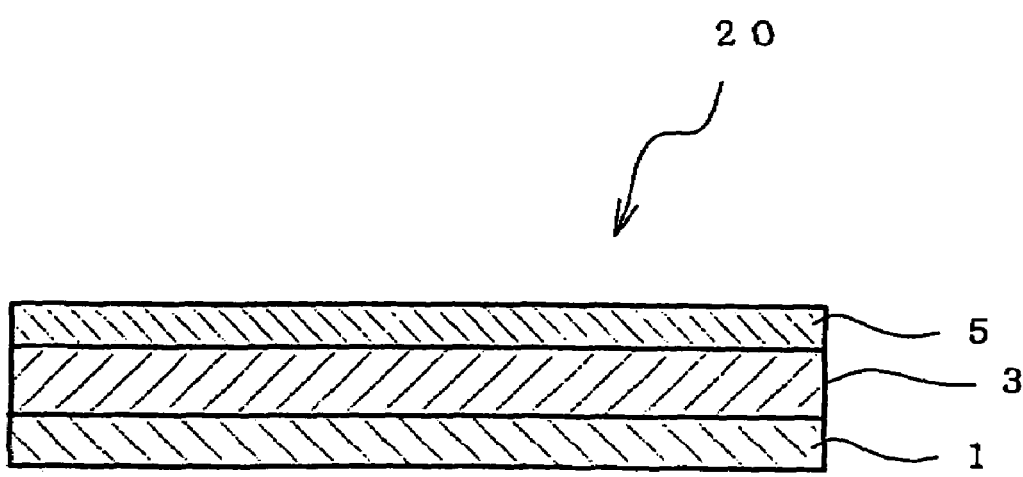
FIG. 2 is a sectional view showing another embodiment of the adhesive preparation of the present invention.

FIG. 1 is a sectional view showing one embodiment of the adhesive preparation of the present invention. An adhesive preparation 10 comprises a support 1 made of a cloth, and a pressure sensitive adhesive layer 3 formed on the support 1. FIG. 2 is a sectional view showing a preferable embodiment of the adhesive preparation of the present invention. An adhesive preparation 20 comprises a support 1 made of a cloth, a pressure sensitive adhesive layer 3 formed on the support 1 and a release sheet 5 formed on the pressure sensitive adhesive layer 3. In an adhesive preparation 20, a release sheet 5 is laminated on the pressure sensitive adhesive layer 3 to prevent the pressure sensitive adhesive layer 3 from adhering to instruments, container and the like during manufacture, transportation and preservation, and prevent degradation of the adhesive preparation 20. When in use, the release sheet 5 is peeled off to expose and adhere an adhesion surface of the pressure sensitive adhesive layer 3 to the skin. In the following, the adhesive preparation 20 is quoted for the explanations. The same applies to the adhesive preparation 10.

In the adhesive preparation 20, a ratio (CW/AW) of a mass (CW) per unit area of the support 1 and a mass (AW) per unit area of the pressure sensitive adhesive layer 3 is 1.0-5.0, preferably 1.5-4.5. As a result, even when a part of a pressure sensitive adhesive is extruded from the periphery of a support 1 due to cold flow, a part of the extruded pressure sensitive adhesive adheres to a part of the side of the support 1 as the adhesive preparation 20 is peeled off from the release sheet 5 for application. Consequently, staining of clothes with a part of the pressure sensitive adhesive attached thereto during application, as well as remainder of a part of the pressure sensitive adhesive on the skin can be prevented. When the support 1 has a given thickness, the pressure sensitive adhesive which may be exposed at the periphery of the adhesive preparation 20 does not easily touch the clothes. Therefore, peeling off or falling off of the adhesive preparation 20 due to adhesion of the pressure sensitive adhesive to a part of the clothes during putting on/taking off of the clothes can be prevented. Furthermore, the cloth constituting the support 1 freely has a number of clearances. Thus, the possibility of a part of a pressure sensitive adhesive extruding from the periphery of the support 1 due to cold flow becomes still lower. When CW/AW becomes less than 1.0, the thickness ratio of the support 1 to pressure sensitive adhesive layer 3 tends to become small. As a result, the side of the support 1 may not be wide enough for a part of the pressure sensitive adhesive extruded due to the cold flow to adhere to, and the part of the pressure sensitive adhesive may attach to the clothes during application, or the part of the pressure sensitive adhesive may remain on the skin during peeling off. On the other hand, when CW/AW exceeds 5.0, the thickness of the support 1 becomes relatively thick and the side thereof becomes easily caught by the clothes. In addition, the thickness of the pressure sensitive adhesive layer 3 becomes relatively thin and skin adhesion decreases. As a result, the adhesive preparation 20 more likely to peel off/fall off along with the movement of the body or during putting on/taking off of the clothes.

While the mass per unit area of the support 1 can be measured according to JIS L 1018:1990, it is preferably 60-160 g/m$^2$, more preferably 80-130 g/m$^2$. When the mass is less than 60 g/m$^2$, the drape property tends to decrease and the handling property tends to be degraded. When it exceeds 160 g/m$^2$, the modulus becomes high, and the stretchability and moisture permeability tend to be degraded, which is economically disadvantageous. The thickness of the support 1 can be measured according to JIS L 1085:1998, and is preferably 150-750 µm, more preferably 200-700 µm. When the thickness of the support 1 is less than 150 µm, the strength becomes insufficient and the operability also tends to be degraded, and bleeding of the pressure sensitive adhesive is also feared. When it exceeds 750 µm, the flexibility and stretchability are degraded, and foreign body sensation may be felt during adhesion due to the thickness. Furthermore, the moisture permeability tends to be degraded, which is economically disadvantageous.

The mass per unit area of the pressure sensitive adhesive layer 3 is preferably 10-150 g/m$^2$, more preferably 30-100 g/m$^2$, in consideration of the adhesiveness, necessary amount and utilization ratio of a drug and the like. When the mass is less than 10 g/m$^2$, sufficient skin adhesion may not be obtained or sufficient pharmacological effect may not be afforded easily. When it exceeds 150 g/m$^2$, utilization ratio of the drug may be degraded and the production cost tends to increase. The mass per unit area of the pressure sensitive adhesive layer 3 can also be measured according to JIS L 1018:1990. The mass per unit area of the support 1 and the mass per unit area of the pressure sensitive adhesive layer 3 are appropriately set to meet a ratio (CW/AW) of 1.0-5.0. The thickness of the pressure sensitive adhesive layer 3 is preferably 5-150 µm, more preferably 10-130 µm. When the thickness of the pressure sensitive adhesive layer 3 is less than 5 µm, sufficient skin adhesion cannot be afforded easily, and peeling off and falling off easily occur during application. When it exceeds 150 µm, a pressure sensitive adhesive easily extrudes from the periphery of the support 1, which may cause strong skin irritation and foreign body sensation during adhesion. The thickness of the pressure sensitive adhesive layer 3 can also be measured according to JIS L 1085:1998.

The static friction coefficient of the pressure sensitive adhesive layer-free surface of the support 1 is 0.25-0.75, preferably 0.3-0.7. Consequently, handling touch can be imparted and peeling off due to friction with the clothes can be prevented. When the static friction coefficient is less than 0.25, the surface becomes slippery during operation, which may cause inconvenience during adhesion. In addition, the anchoring effect with the pressure sensitive adhesive layer 3 becomes insufficient and the completeness of an adhesive preparation becomes low. When it exceeds 0.75, the friction with clothes increases and the adhesive preparation more likely to peel off/fall off along with the movement of the body or during putting on/taking off of the clothes. Here, in the present specification, the "static friction coefficient" is a value measured by the test method described in JIS P 8147:1994 (according to friction coefficient test method of paper and cardboard).

Moreover, the adhesive preparation 20 shows a 20% modulus (AM) in any one direction and a 20% modulus (EM) in the direction perpendicular to said direction each of 0.5-1.5 N/cm. The ratio thereof (AM/EM) is 0.5-2.0, preferably 0.7-1.3. This has an effect of comfortable feeling of adhesion and superior skin followability. When AM and EM are less than 0.5 N/cm, the strength becomes insufficient, peeling off due to breakage and destruction tends to occur during adhesion, and toughness decreases to cause difficulty in operation. When it exceeds 1.5, the followability to skin deformation becomes insufficient and foreign body sensation occurs during adhesion. In addition, the periphery of the adhesive preparation 20 easily peels off at the bending part. When AM/EM is less than 0.5 or exceeds 2.0, foreign body sensation occurs during adhesion and peeling off and falling off easily occur due to bending. In the present specification, the "20% modulus" means a value measured according to the test method described in JIS Z 0237:2000 (according to tensile strength and elongation of the pressure-sensitive adhesive tape•pressure-sensitive adhesive sheet test method). The 50% modulus generally used for the evaluation of stretchability and flexibility is unsuitable for precisely measuring the stretchability of the support 1 in the present invention, because measurement is mostly done in the area where elasticity has disappeared.

Moreover, the shear adhesive force of the adhesive preparation 20 is preferably 1.0-7.0 N/cm, more preferably 1.5-6.5 N/cm, from the aspects of decreased physical stimuli during peeling off, decreased foreign body sensation during adhesion, and difficult peeling off at the bending part. When the shear adhesive force is less than 1.0 N/cm, the periphery tends to be peeled off at the bending part. When it exceeds 7.0 N/cm, peeling off of the adhesive preparation 20 becomes painful, physical stimuli cause skin disorders, and suppressed elongation of the skin during adhesion easily causes foreign body sensation. In the present specification, the "shear adhesive force" is a value measured according to the test method described in JIS Z 0237:1991 (according to the method of Reference 3 of the pressure-sensitive adhesive tape·pressure-sensitive adhesive sheet test method).

The amount of moisture permeation of the adhesive preparation 20 is preferably 500-3000 $g/cm^2 \cdot 24$ hr, more preferably 800-2000 $g/cm^2 \cdot 24$ hr, because peeling off and sweat pool due to perspiration, and insufficient pharmacological effect and skin disorders such as skin irritation and the like, which are caused thereby, can be suppressed, and a therapeutic or prophylactic effect can be achieved by an appropriate occlusive dressing technique (ODT) effect. When the amount of moisture permeation is less than 500 $g/cm^2 \cdot 24$ hr, the moisture resulting from the perspiration cannot be evaporated easily from between the skin and the surface of the pressure sensitive adhesive layer 3, thus leading to peeling off of the adhesive preparation 20 and sweat pool, which in turn easily degrades pharmacological effects and causes skin disorders such as skin irritation and the like. On the other hand, when the amount of moisture permeation exceeds 3000 $g/cm^2 \cdot 24$ hr, an appropriate ODT effect is difficult to achieve and a therapeutic or prophylactic effect due to a drug tends to decrease. The amount of moisture permeation can be appropriately controlled depending on the mass per unit area of the support 1, thickness of the support 1, area of the adhesive preparation 20, monomer composition ratio of the copolymer forming the pressure sensitive adhesive layer 3, kind and content ratio of the below-mentioned organic liquid components, mass per unit area of the pressure sensitive adhesive layer 3 and the like. In addition, the amount of moisture permeation of the cloth itself is preferably not less than 5000 $g/m^2 \cdot 24$ hr, more preferably not less than 7000 $g/m^2 \cdot 24$ hr. When the amount of moisture permeation is less than 5000 $g/m^2 \cdot 24$ hr, sufficient moisture permeability cannot be achieved easily when the pressure sensitive adhesive layer 3 is laminated. Moreover, the amount of moisture permeation of the adhesive preparation is desirably adjusted to 5-25%, preferably 8-20%, relative to the amount of moisture permeation inherent of the cloth constituting the support 1. When the ratio exceeds 25%, an appropriate ODT effect cannot be obtained easily and a therapeutic or prophylactic effect due to a drug tends to decrease. On the other hand, when it is less than 5%, the porosity of the cloth cannot be significantly utilized and a sufficient effect cannot be obtained easily. In the present specification, the "amount of moisture permeations" is a value measured according to the method described in JIS L 1099:1993 (according to calcium chloride method of the degree of moisture permeation test method for fiber products).

The adhesiveness of the adhesive preparation 20 to a bakelite plate is preferably 0.1-0.7 N/24 mm width, more preferably 0.15-0.6 N/24 mm width, from the aspects of reduction of pain and physical stimuli upon peeling off, reduction of foreign body sensation during adhesion, and stable long-term adhesion. When the adhesiveness is less than 0.1 N/24 mm width, adhesion to the skin becomes insufficient and peeling off and falling off may occur during application. When it exceeds 0.7 N/24 mm width, skin disorders due to pain and physical stimuli upon peeling off easily occur. While the conventionally used adhesive tapes mostly have adhesiveness greater that that, since the adhesive preparation 20 can follow, together with the support 1 and pressure sensitive adhesive layer 3, even a soft and minute deformation, a substantial skin adhesion area becomes large and good skin adhesion can be achieved. In the present specification, the "adhesion" refers to a value measured according to the method described in JIS Z 0237:2000 (according to adhesive force of the pressure-sensitive adhesive tape·pressure-sensitive adhesive sheet test method). That is, the adhesive preparation 20 is cut into a sample band having a width of 24 mm, adhered to a bakelite plate (thickness 2 mm, width 50 mm, length 130 mm) and pressed by one reciprocation with a roller (load 850 g). After press adhesion, the adhesive preparation is left standing at 23° C. for 20 min, peeled off in the 180-degree direction with a TENSILON type tensile tester at 300 mm/min under the same atmosphere. The value measured as a release force here is the value mentioned above.

In the present specification, the "cloth" refers to a sheet-like fiber assembly formed by knitting, weaving, interlacing and the like of a chemical fiber or natural fiber, which may take any form of knitted fabric, woven fabric, non-woven fabric and the like. Of these, a knitted fabric is preferable in view of handling touch, flexibility, elasticity and uniformity.

While the method of forming a knitted fabric is not particularly limited as long as stretchability and elasticity can be maintained, warp knitting is preferable and circular knitting and weft knitting are more preferable.

A cloth to be used for the support 1 is not particularly limited as long as the preparation satisfies the aforementioned mass per unit area, static friction coefficient and 20% modulus within the above-mentioned predetermined numerical values. For example, natural fibers such as cotton, hemp, silk, wool and the like, recycled fibers such as viscose rayon, cuprammonium rayon and the like, semi-synthetic fibers such as promix, diacetate, triacetate and the like, and synthetic fibers such as nylon, vinylon, vinylidene, polyvinyl chloride, polyethylene terephthalate, polybutylene terephthalate, polyethylene, polypropylene, polyurethane, benzoate, polycral and the like can be used. In consideration of the stability, safety, uniformity, economical aspect, processability, drug non-immigration and the like, synthetic fibers are preferable, polyester and polyolefin are more preferable, and polyethylene terephthalate is still more preferable. The fiber preferably has an about circular cross sectional shape having a diameter of 10-30 μm, more preferably 15-25 μm, from the aspects of versatility, economical aspect and processability. In addition, a composite fiber may be used.

The pressure sensitive adhesive layer 3 is preferably made of a medical adhesive as a main component, which is conventionally used as a pressure sensitive adhesive that does not easily cause skin irritation and the like when applied to the skin. As such medical adhesive, acrylic adhesive, natural rubber adhesive, synthetic rubber adhesive, silicone adhesive, vinyl ester adhesive, vinyl ether adhesive and the like can be mentioned. Of these, an acrylic adhesive is preferable from the aspects of stable quality, adhesive property and easy control of moisture permeation of the adhesive.

The acrylic adhesive preferably contains a copolymer obtained by copolymerizing a (meth)acrylic acid alkyl ester (main component) with a copolymerizable monomer. Since this acrylic copolymer can be crosslinked with a crosslinking agent, decrease or disappearance of adhesiveness, which is caused by penetration of the copolymer through clearance between knitted stitches and fibers of the cloth over time when applied to the support 1, can be prevented. As the (meth)acrylic acid alkyl ester, an ester of primary to tertiary alcohols having alkyl group having 2-18 carbon atoms, preferably 4-12 carbon atoms, with acrylic acid or methacrylic acid can be mentioned. One or more kinds of (meth)acrylic acid alkyl esters can be used in combination.

As the monomer copolymerizable with (meth)acrylic acid alkyl ester, a functional monomer containing at least one addition polymerizable unsaturated double bond in a molecule and a functional group such as carboxyl group, hydroxyl group, sulfoxyl group, amino group, amide group, alkoxyl group and the like on the side chain can be mentioned. As the carboxyl group-containing monomer, (meth)acrylic acid, itaconic acid, maleic acid, maleic anhydride and the like can be mentioned. As the hydroxyl group-containing monomer, (meth)acrylic acid hydroxyethyl ester, (meth)acrylic acid hydroxypropyl ester and the like can be mentioned. As the sulfoxyl group-containing monomer, styrene sulfonic acid, allyl sulfonic acid, (meth)acrylic acid sulfopropyl ester, (meth)acryloyloxynaphthalene sulfonic acid, acrylamidomethylpropanesulfonic acid and the like can be mentioned. As the amino group-containing monomer, (meth)acrylic acid aminoethyl ester, (meth)acrylic acid dimethylaminoethyl ester, (meth)acrylic acid tertbutylaminoethyl ester and the like can be mentioned. As the amide group-containing monomer, (meth)acrylamide, dimethyl(meth)acrylamide, N-butylacrylamide, N-methylol(meth)acrylamide, N-methylolpropane(meth)acrylamide and the like can be mentioned. As the alkoxyl group-containing monomer, (meth)acrylic acid methoxyethyl ester, (meth)acrylic acid ethoxyethyl ester, (meth)acrylic acid methoxyethyleneglycol ester, (meth)acrylic acid methoxydiethyleneglycol ester, (meth)acrylic acid methoxypolyethyleneglycol ester, (meth)acrylic acid ethoxypolyethyleneglycol ester, (meth)acrylic acid tetrahydrofurfuryl ester and the like can be mentioned.

Besides these, as a copolymerizable monomer other than the above, for example, (meth)acrylonitrile, vinyl acetate, vinyl propionate, N-vinyl-2-pyrrolidone, N-vinylacetamide, methylvinylpyrrolidone, vinylpyridine, vinylpiperidone, vinylpyrimidine, vinylpiperazine, vinylpyrazine, vinylpyrrole, vinylimidazole, vinylcaprolactam, vinyloxazole and vinylmorpholine can be mentioned. One or more kinds of these copolymerizable monomers can be used in combination. In consideration of the adhesiveness, coagulation property, control of moisture permeation and the like, it is preferable to copolymerize at least one of carboxyl group-containing monomer, alkoxyl group-containing monomer and hydroxyl group-containing monomer as an essential component and, where necessary, other monomers exemplified above.

The acrylic copolymer preferably contains (meth)acrylic acid alkyl ester in a proportion of not less than 40 mass %, and a copolymer obtained by copolymerizing (meth)acrylic acid alkyl ester (50-99.5 mass %, preferably 60-97 mass %) with the aforementioned copolymerizable monomer (0.5-50 mass %, preferably 2-10 mass %) is more preferable. Specifically, a copolymer of (meth)acrylic acid 2-ethylhexyl ester and (meth)acrylic acid, and a copolymer of (meth)acrylic acid 2-ethylhexyl ester (40-99.5 mass %, preferably 60-97 mass %), (meth)acrylic acid (0.5-50 mass %, preferably 2-10 mass %) and N-vinyl-2-pyrrolidone (5-50 mass %, preferably 10-40 mass %) can be mentioned. The acrylic copolymer can be synthesized using (meth)acrylic acid alkyl ester and the aforementioned copolymerizable monomer by a known radical polymerization method such as solution polymerization method, emulsion polymerization method, mass polymerization method, suspension polymerization method and the like.

While the pressure sensitive adhesive can consist of the aforementioned copolymer alone, it can contain an organic liquid component compatible with the copolymer. The organic liquid component reduces physical skin irritation by imparting softness to the pressure sensitive adhesive layer 3 upon plasticizing the copolymer, and also enables control of the moisture permeability. The organic liquid component is not particularly limited as long as it is liquid at room temperature, has a plasticizing action and is compatible with the aforementioned copolymer, with preference given to one that improves transdermal absorbability and preservation stability of a drug. Specifically, fatty acid ester obtained from a higher fatty acid having 12-16 (preferably 12-14) carbon atoms and a lower monohydric alcohol having 1-4 carbon atoms; fatty acid having 8-10 carbon atoms; glycols such as ethylene glycol, diethylene glycol, triethylene glycol, polyethylene glycol, propylene glycol, polypropylene glycol and the like; fats and oils such as olive oil, castor oil, squalene, lanoline and the like; organic solvents such as ethyl acetate, ethyl alcohol, dimethyldecyl sulfoxide, methyloctyl sulfoxide, dimethyl sulfoxide, dimethylformamide, dimethylacetamide, dimethyllaurylamide, dodecylpyrrolidone, isosorbitol and the like; liquid surfactants; conventionally known plasticizers such as diisopropyl adipate, phthalic acid ester, diethyl sebacate and the like; hydrocarbons such as liquid paraffin and the like; and ethoxylated stearyl alcohol, glycerol fatty acid ester (liquid at room temperature), sorbitan fatty acid ester, isopropyl myristate, isotridecyl myristate, ethyl laurate, N-methyl-2-pyrrolidone, ethyl oleate, oleic acid, diisopropyl adipate, diisopropyl palmitate, octyl palmitate, 1,3-propanediol, glycerol and the like can be mentioned. One or more kinds of these can be used in combination.

Of the above-mentioned organic liquid components, fatty acid ester is preferably used in view of compatibility with copolymer, reduction of skin stimuli, appropriate skin adhesion, no volatilization in heating step and the like. As a higher fatty acid constituting the fatty acid ester, lauric acid (C12), myristic acid (C14) and palmitic acid (C16) are preferable, and myristic acid is particularly preferable. As the lower monohydric alcohol, methyl alcohol, ethyl alcohol, propyl alcohol, butyl alcohol and the like can be mentioned. These are not limited to straight chain alcohols and may be branched alcohols. Of these, isopropyl alcohol is preferable as the lower monohydric alcohol. As the fatty acid ester, isopropyl myristate is most preferable. The content of the organic liquid component is preferably 10-150 parts by mass, more preferably 50-120 parts by mass, per 100 parts by mass of the above-mentioned copolymer. When the content is less than 10 parts by mass, the pressure sensitive adhesive layer 3 is insufficiently plasticized and physical skin irritation may not be sufficiently reduced. When it exceeds 150 parts by mass, the organic liquid component may not be sufficiently maintained in the pressure sensitive adhesive layer 3 even if the coagulation of the copolymer is sufficient, and the organic liquid component may bloom on the surface of the pressure sensitive adhesive layer 3 to degrade adhesiveness.

The pressure sensitive adhesive. layer 3 may be crosslinked with a crosslinking agent to give a gel. This has an effect that fatty acid ester added is not effluxed and imparts cohesion. The crosslinking treatment can be carried out, for example, using a crosslinking agent such as polyisocyanate compound, organic peroxide, organic metal salt, metal alcolate, metal chelate compound, multifunctional. compound and the like. Of these crosslinking agents, trifunctional isocyanate and aluminum chelate compound are preferable in view of the crosslinking reactivity and handling property. These crosslinking agents are extremely superior in workability, because they are nearly free from thickening of solution before coating and drying. The content of the crosslinking agent is generally 0.01-2 parts by mass, preferably 0.05-1.5 parts by mass, per 100 parts by mass of the copolymer.

The drug to be contained in the pressure sensitive adhesive layer 3 is not particularly limited as long as it shows transdermal absorbability, and is appropriately selected according to the treatment objects. Specific examples thereof include sedative hypnotics such as alprazolam, diazepam, nitrazepam, fludiazepam, phenobarbital and the like, anti-anxiety agent, antiepileptic agents such as phenytoin, trimethadione, ethosuximide, zonisamide, clobazam and the like, antipyretics, antiphlogistics and analgesics such as methyl salicylate, glycol salicylate, acetaminophen, mefenamic acid, indomethacin, ketoprofen, flurbiprofen, loxoprofen, piroxicam and the like, antiparkinson agents such as amantadine, biperiden, levodopa, selegiline, trihexyphenidyl, pergolide, talipexole and the like, psychoneurotic agents such as chlorpromazine, perphenazine, imipramine, etizolam, perospirone, baroxetine, methylphenidate, olanzapine, sulpiride, haloperidol and the like, local anesthetics such as lidocaine, oxethazaine, procaine, dibucaine, bupivacaine, mepivacaine, robivacaine, benzocaine and the like, skeletal muscle relaxants such as chlorzoxazone, chlorphenesin, suxamethonium, vecuronium and the like, autonomic agents such as carpronium, bethanechol, neostigmine, dicycloverine, pyridostigmine and the like, antispasmodic agents such as scopolamine, atropine, papaverine, eperisone, tizanidine, baclofen and the like, cardiotonic agents such as digitoxin, digoxin, aminophylline, caffeine, etilefrine and the like, arrhythmic agents such as procainamide, quinidine, atenolol, propranolol, pindolol and the like, diuretics such as spironolactone, acetazolamide, furosemide and the like, antihypertensive agents such as hydralazine, reserpine, imidapril, enalapril, lisinopril, clonidine, nicardipine, terazosin, bunitrolol and the like, vasoconstrictors such as midodrine and the like, vasodilators such as isosorbide, dilazep, diltiazem, nicorandil, nitroglycerol, nifedipine and the like, antilipemic agents such as clofibrate, estase, pravastatin, nicomol, probucol and the like, antitussives such as ephedrine, noscapine, dextromethorphan, fominoben, dimemorfan and the like, antitussive expectorants such as codeine, dihydrocodeine, tipepidine and the like, bronchodilators such as theophylline, terbutaline, tulobuterol, clenbuterol, salbutamol, procatetol and the like, gastric ulcer agents such as cimetidine, ranitidine, aldioxa, pirenzepine, irsogladine and the like, hormone agents such as liothyronine, levothyroxine, hydrocortisone, dexamethasone, prednisolone, methyltestosterone, ethinylestradiol and the like, oxytocics such as ergometrine and the like, genitourinary and anal drugs such as oxybutynin, tamsulosin, flavoxate, ritodrine and the like, vitamins such as alfa calcidol, carcitriol, thiamin, riboflavin, pyridoxine, mecobalamin, ascorbic acid, tocopherol and the like, locally stimulating agents such as capsaicin, nonylic acid vanillylamide, dihydrocapsaicin, capsiate, menthol, menthone, camphor, gingerol, gingerone and the like, agents for liver diseases such as glucuronolactone, aminoethylsulfonic acid and the like, antidotes such as glutathione, trientine, penicillamine and the like, agents for habitual intoxication such as cyanamide, disulfiram and the like, therapeutic agents for gout such as colchicine, probenecid, allopurinol, benzbromarone and the like, enzyme preparations such as lysozyme chloride, serrapeptase and the like, diabetic agents such as acetohexamide, glibenclamide, tolbutamide, acarbose and the like, metabolic pharmaceutical agents such as sodium chondroitin sulfate, azathioprine, cyclosporin, tacrolimus, camostat and the like, alkylating agents such as cyclophosphamide, melphalan, carboquone and the like, metabolic antagonists such as mercaptopurine, tegafur, fluorouracil and the like, plant-derived antitumor preparations such as etoposide and the like, antitumor agents such as anastrozole, fadrozole, sobuzoxane, bicalutamide and the like, antihistaminic agents such as diphenhydramine, promethazine, mequitazine, chlorpheniramine, clemastine and the like, anti-allergic agents such as ibudilast, azelastine, oxatomide, tranilast, ketotifen and the like, antibiotics such as clindamycin, fradiomycin, amoxicillin, ampicillin, cefaclor, cefalexin, erythromycin, minocycline and the like, sulfa drugs such as sulfamethoxazole, sufamethizol and the like, antituberculous agents such as isoniazid, pyrazinamide, ethambutol and the like, synthetic antibacterial agents such as enoxacin, ofloxacin, nalidixic acid, norfloxacin and the like, antiviral agents such as acyclovir, gancyclovir, didanosine, lamivudine and the like, chemotherapeutic agents such as terbinafine, itraconazole, miconazole and the like, antiprotozoal agents such as quinine, metronidazole and the like, anthelmintic agents such as thymol, santonin, thiabendazole and the like, narcotics such as morphine, ethylmorphine, codeine, oxycodon, fentanil, sufentanil, remifentanil, levallorphan and the like, coca alkaloid drugs such as cocaine and the like, stimulant drugs such as methamphetamine and the like, and the like. The above-mentioned drugs include inorganic salts and organic salts that can be substantially prepared. One or more kinds of these drugs are used in combination.

While the content of the drug in the pressure sensitive adhesive layer 3 is appropriately determined depending on the kind of percutaneously absorbable drug and administration object, it is preferably 0.01-60 mass %, more preferably 0.1-30 mass %. When the content is less than 0.01 mass %, release of the drug in an amount effective for the treatment cannot be expected, and when it exceeds 60 mass %, a therapeutic or prophylactic effect corresponding to the content cannot be obtained easily, which is economically disadvantageous.

Where necessary, the pressure sensitive adhesive layer 3 may contain, besides a pressure sensitive adhesive and a drug, known additives such as adhesion imparting agents (e.g., rosin, modified rosin, petroleum resin, polyterpene resin, polystyrene resin, polybutene resin, liquid polyisobutylene etc.), plasticizers (e.g., liquid paraffin etc.), absorption promoters, surfactants (e.g., sorbitan trioleate etc.), fillers, antioxidants (e.g., propyl gallate, 2-mercaptobenzimidazole etc.) and the like.

The release sheet 5 is not particularly limited as long as it can be easily peeled off from the pressure sensitive adhesive layer 3 during use. For example, films of polyester, polyvinyl chloride, polyvinylidene chloride, polyethylene terephthalate and the like, wherein the contact surface with the pressure sensitive adhesive layer 3 is treated with silicone, a laminate film of quality paper or glassine with polyolefin and the like are used. The thickness of the release sheet 5 is generally not more than 1000 μm, preferably 30-200 μm. In addition, the release sheet 5 may have suitable cuts to facilitate the adhesion operation.

The production method of the adhesive preparation 20 is not particularly limited. For example, an acrylic copolymer, the aforementioned organic liquid component, a drug and a crosslinking agent are dissolved or dispersed in a solvent in this order, the obtained solution or dispersion is applied to a protective release sheet and dried to form a pressure sensitive adhesive layer on the release sheet, a support is adhered to the pressure sensitive adhesive layer, which is heated at a suitable temperature for a given time to perform a crosslinking reaction, and the pressure sensitive adhesive layer 3 is turned into a gel to give an adhesive preparation. While the size of the adhesive preparation 20 varies depending on the therapeutic use and object of use, it is generally 10-300 cm$^2$, preferably 20-200 cm$^2$. Where necessary, the edge may have a circular arc having a suitable radius of curvature.

While the dose of the adhesive preparation 20 varies depending on the age, body weight, symptom etc. of the patients, it is preferable to generally apply the adhesive preparation 20 containing 0.001-100 mg of a drug per one application to the skin of the chest, abdomen, back, arm, leg, face and the like or mucous membrane of an adult about 1 or 2 times in 1 to 7 days.

EXAMPLES

The present invention is explained in detail in the following by referring to Examples, which are not to be construed as limitative.

(Preparation of Copolymer A Solution)

2-Ethylhexyl acrylate (95 parts by mass), acrylic acid (5 parts by mass), ethyl acetate (100 parts by mass) and benzoyl peroxide (0.2 parts by mass) were reacted in a separable flask equipped with a refluxing condenser, a stirrer, a thermometer, a dropping funnel and a nitrogen inlet tube under a nitrogen atmosphere at 60° C. for 15 hr to give a solution of copolymer A.

(Preparation of Copolymer B Solution)

2-Ethylhexyl acrylate (72 parts by mass), N-vinyl-2-pyrrolidone (25 parts by mass), acrylic acid (3 parts by mass), ethyl acetate (333 parts by mass) and azobisisobutyronitrile (0.2 parts by mass) were reacted in a separable flask equipped with a refluxing condenser, a stirrer, a thermometer, a dropping funnel and a nitrogen inlet tube under a nitrogen atmosphere at 60° C. for 6 hr and then at 76° C. for 18 hr to give a solution of copolymer B.

(Preparation of Polyisobutylene Solution)

High molecular weight polyisobutylene (28.5 parts, VISTANEX MML-80, viscosity average molecular weight 990,000, manufactured by BASF), low molecular weight polyisobutylene (43 parts, HIMOL 6H, viscosity average molecular weight 60,000, manufactured by Nippon Petrochemicals Company, Limited), polybutene (8.5 parts, HV-300, viscosity average molecular weight 1,260, manufactured by Nippon Petrochemicals Company, Limited), and alicyclic petroleum resin (20 parts, ARKON P-100, softening point 100° C.; manufactured by Arakawa Chemical Industries, Ltd.) were dissolved in hexane to give a polyisobutylene solution.

Example 1

To the above-mentioned solution of copolymer A, which has a solid content corresponding to 12 g, were added isopropyl myristate (8 g), glycol salicylate (2 g), trifunctional isocyanate (0.0108 g, CORONATE HL, manufactured by Nippon Polyurethane Industry Co., Ltd.) as a crosslinking agent and a suitable amount of ethyl acetate for adjusting the concentration, and the mixture was stirred to give a homogeneous pressure sensitive adhesive solution containing a drug and having a non-solvent concentration of 30 mass %. The obtained pressure sensitive adhesive solution was applied onto a 75 μm-thick polyester release sheet to a mass per unit area after drying of 60 g/m$^2$, and dried to give a crosslinked gel-like pressure sensitive adhesive layer. The pressure sensitive. adhesive layer prepared above was transferred and laminated on an about 400 μm-thick circular knitted fabric A having a mass per unit area of 105 g/m$^2$, which was prepared from a polyester fiber having a diameter of about 20 μm and an about circular section, and the laminate was packaged with an aluminum laminate film and aged at 70° C. for 48 hr. Furthermore, the laminate sheet after aging was cut to give an adhesive preparation (length 10 cm, width 14 cm, an edge being a circular arc with a curvature radius of 1 cm).

Example 2

To the above-mentioned solution of copolymer B, which has a solid content corresponding to 9 g, were added isopropyl myristate (11 g), glycol salicylate (2 g), trifunctional isocyanate (0.036 g, CORONATE HL, manufactured by Nippon Polyurethane Industry Co., Ltd.) as a crosslinking agent and a suitable amount of ethyl acetate for adjusting the concentration, and the mixture was stirred to give a homogeneous pressure sensitive adhesive solution containing a drug and having a non-solvent concentration of 30 mass %. The obtained pressure sensitive adhesive solution was applied onto a 75 μm-thick polyester release sheet to a mass per unit area after drying of 60 g/m$^2$, and dried to give a crosslinked gel-like pressure sensitive adhesive layer. The pressure sensitive adhesive layer prepared above was transferred and laminated on an about 400 μm-thick circular knitted fabric A having a mass per unit area of 105 g/m², which was prepared from a polyester fiber having a diameter of about 20 μm and an about circular section, and the laminate was packaged with an aluminum laminate film and aged at 70° C. for 48 hr. Furthermore, the laminate sheet after aging was cut to give an adhesive preparation (length 10 cm, width 14 cm, an edge being a circular arc with a curvature radius of 1 cm).

Example 3

To the above-mentioned solution of polyisobutylene, which has a solid content corresponding to 16 g, were added isopropyl myristate (3 g) and glycol salicylate (1 g) a suitable amount of a mixture of hexane/tetrahydrofuran (1:1) for adjusting the concentration, and the mixture was stirred to give a homogeneous pressure sensitive adhesive solution containing a drug and having a non-solvent concentration of 20 mass %. The obtained pressure sensitive adhesive solution was applied onto a 75 μm-thick polyester release sheet to a mass per unit area after drying of 60 g/m², and dried to give a crosslinked gel-like pressure sensitive adhesive layer. The pressure sensitive adhesive layer prepared above was transferred and laminated on an about 400 μm-thick circular knitted fabric having a mass per unit area of 105 g/m², which was prepared from a polyester fiber having a diameter of about 20 μm and an about circular section. Furthermore, the laminate sheet was cut to give an adhesive preparation (length 10 cm, width 14 cm, an edge being a circular arc with a curvature radius of 1 cm).

Example 4

To the above-mentioned solution of copolymer A, which has a solid content corresponding to 10 g, were added isopropyl myristate (8 g), glycol salicylate (2 g), trifunctional isocyanate (0.0108 g, CORONATE HL, manufactured by Nippon Polyurethane Industry Co., Ltd.) as a crosslinking agent and a suitable amount of ethyl acetate for adjusting the concentration, and the mixture was stirred to give a homogeneous pressure sensitive adhesive solution containing a drug and having a non-solvent concentration of 30 mass %. The obtained pressure sensitive adhesive solution was applied onto a 75 μm-thick polyester release sheet to a mass per unit area after drying of 60 g/m², and dried to give a crosslinked gel-like pressure sensitive adhesive layer. The pressure sensitive adhesive layer prepared above was transferred and laminated on an about 550 μm-thick circular knitted fabric B having a mass per unit area of 150 g/m², which was prepared from a polyester fiber having a diameter of about 20 μm and an about circular section, and the laminate was packaged with an aluminum laminate film and aged at 70° C. for 48 hr. Furthermore, the laminate sheet after aging was cut to give an adhesive preparation (length 10 cm, width 14 cm, an edge being a circular arc with a curvature radius of 1 cm).

Example 5

To the above-mentioned solution of copolymer B, which has a solid content corresponding to 9 g, were added isopropyl myristate (11 g), glycol salicylate (2 g), trifunctional isocyanate (0.036 g, CORONATE HL, manufactured by Nippon Polyurethane Industry Co., Ltd.) as a crosslinking agent and a suitable amount of ethyl acetate for adjusting the concentration, and the mixture was stirred to give a homogeneous pressure sensitive adhesive solution containing a drug and having a non-solvent concentration of 30 mass %. The obtained pressure sensitive adhesive solution was applied onto a 75 μm-thick polyester release sheet to a mass per unit area after drying of 40 g/m², and dried to give a crosslinked gel-like pressure sensitive adhesive layer. The pressure sensitive adhesive layer prepared above was transferred and laminated on a 400 μm-thick spunlaced non-woven fabric having a mass of 60 g/m², which was prepared from a composite fiber made of a polyester fiber (60%) and a rayon fiber (40%) having a diameter of about 5-10 μm and an about triangle section, and the laminate was packaged with an aluminum laminate film and aged at 70° C. for 48 hr. Furthermore, the laminate sheet after aging was cut to give an adhesive preparation (length 10 cm, width 14 cm, an edge being a circular arc with a curvature radius of 1 cm).

Example 6

To the above-mentioned solution of copolymer A, which has a solid content corresponding to 12 g, were added isopropyl myristate (8 g), flurbiprofen (1 g), trifunctional isocyanate (0.0108 g, CORONATE HL, manufactured by Nippon Polyurethane Industry Co., Ltd.) as a crosslinking agent and a suitable amount of ethyl acetate for adjusting the concentration, and the mixture was stirred to give a homogeneous pressure sensitive adhesive solution containing a drug and having a non-solvent concentration of 30 mass %. The obtained pressure sensitive adhesive solution was applied onto a 75 μm-thick polyester release sheet to a mass per unit area after drying of 60 g/m², and dried to give a crosslinked gel-like pressure sensitive adhesive layer. The pressure sensitive adhesive layer prepared above was transferred and laminated on an about 400 μm-thick circular knitted fabric A having a mass per unit area of 105 g/m², which was prepared from a polyester fiber having a diameter of about 20 μm and an about circular section, and the laminate was packaged with an aluminum laminate film and aged at 70° C. for 48 hr. Furthermore, the laminate sheet after aging was cut to give an adhesive preparation (length 10 cm, width 14 cm, an edge being a circular arc with a curvature radius of 1 cm).

Example 7

To the above-mentioned solution of copolymer A, which has a solid content corresponding to 12 g, were added isopropyl myristate (8 g), capsaicin (0.5 g), trifunctional isocyanate (0.0108 g, CORONATE HL, manufactured by Nippon Polyurethane Industry Co., Ltd.) as a crosslinking agent and a suitable amount of ethyl acetate for adjusting the concentration, and the mixture was stirred to give a homogeneous pressure sensitive adhesive solution containing a drug and having a non-solvent concentration of 30 mass %. The obtained pressure sensitive adhesive solution was applied onto a 75 μm-thick polyester release sheet to a mass per unit area after drying of 60 g/m², and dried to give a crosslinked gel-like pressure sensitive adhesive layer. The pressure sensitive adhesive layer prepared above was transferred and laminated on an about 400 μm-thick circular knitted fabric A having a mass per unit area of 105 g/m², which was prepared from a polyester fiber having a diameter of about 20 μm and an about circular section, and the laminate was packaged with an aluminum laminate film and aged at 70° C. for 48 hr. Furthermore, the laminate sheet after aging was cut to give an adhesive preparation (length 10 cm, width 14 cm, an edge being a circular arc with a curvature radius of 1 cm).

Example 8

To the above-mentioned solution of copolymer A, which has a solid content corresponding to 12 g, were added isopropyl myristate (8 g), capsaicin (0.5 g), trifunctional isocyanate (0.0108 g, CORONATE HL, manufactured by Nippon Polyurethane Industry Co., Ltd.) as a crosslinking agent and a suitable amount of ethyl acetate for adjusting the concentration, and the mixture was stirred to give a homogeneous pressure sensitive adhesive solution containing a drug and having a non-solvent concentration of 30 mass %. The obtained pressure sensitive adhesive solution was applied onto a 75 μm-thick polyester release sheet to a mass per unit area after drying of 60 g/m$^2$, and dried to give a crosslinked gel-like pressure sensitive adhesive layer. The pressure sensitive adhesive layer prepared above was transferred and laminated on an about 400 μm-thick circular knitted fabric having a mass per unit area of 105 g/m$^2$, which was prepared from a polyester fiber having a diameter of about 20 μm and an about circular section, and the laminate was packaged with an aluminum laminate film and aged at 70° C. for 48 hr. Furthermore, the laminate sheet after aging was cut to give an adhesive preparation (length 10 cm, width 14 cm, an edge being a circular arc with a curvature radius of 1 cm).

Example 9

To the above-mentioned solution of copolymer B, which has a solid content corresponding to 10 g, were added and mixed ketoprofen (0.66 g), isopropyl myristate (12 g) and isopropanol. (20 g). To this solution was added ethyl acetoacetate aluminum diisopropylate (0.3 g) as a 5% isopropanol/ ethyl acetoacetate (9/1 (v/v)) solution, and the mixture was stirred to give a homogeneous pressure sensitive adhesive solution containing a drug and having a non-solvent concentration of 25 mass %. The obtained pressure sensitive adhesive solution was applied onto a 75 μm-thick polyester release sheet to a mass per unit area after drying of 60 g/m$^2$, and dried to give a crosslinked gel-like pressure sensitive adhesive layer. The pressure sensitive adhesive layer prepared above was transferred and laminated on an about 400 μm-thick circular knitted fabric having a mass per unit area of 105 g/m$^2$, which was prepared from a polyester fiber having a diameter of about 20 μm and an about circular section, and the laminate was packaged with an aluminum laminate film and aged at 70° C. for 48 hr. Furthermore, the laminate sheet after aging was cut to give an adhesive preparation (length 10 cm, width 14 cm, an edge being a circular arc with a curvature radius of 1 cm).

Example 10

The pressure sensitive adhesive solution containing a drug, which was obtained in the same manner as in Example 1 was applied onto a 75 μm-thick polyester release sheet to a mass per unit area after drying of 20 g/m$^2$, and dried to give a crosslinked gel-like pressure sensitive adhesive layer. The pressure sensitive adhesive layer prepared above was transferred and laminated on an about 400 μm-thick circular knitted fabric having a mass per unit area of 105 g/m$^2$, which was prepared from a polyester fiber having a diameter of about 20 μm and an about circular section, and the laminate was packaged with an aluminum laminate film and aged at 70° C. for 48 hr. Furthermore, the laminate sheet after aging was cut to give an adhesive preparation (length 10 cm, width 14 cm, an edge being a circular arc with a curvature radius of 1 cm).

Example 11

The pressure sensitive adhesive solution containing a drug, which was obtained in the same manner as in Example 1 was applied onto a 75 μm-thick polyester release sheet to a mass per unit area after drying of 40 g/m$^2$, and dried to give a crosslinked gel-like pressure sensitive adhesive layer. The pressure sensitive adhesive layer prepared above was transferred and laminated on an about 400 μm-thick circular knitted fabric having a mass per unit area of 105 g/m$^2$, which was prepared from a polyester fiber having a diameter of about 20 μm and an about circular section, and the laminate was packaged with an aluminum laminate film and aged at 70° C. for 48 hr. Furthermore, the laminate sheet after aging was cut to give an adhesive preparation (length 10 cm, width 14 cm, an edge being a circular arc with a curvature radius of 1 cm).

Example 12

The pressure sensitive adhesive solution containing a drug, which was obtained in the same manner as in Example 1 was applied onto a 75 μm-thick polyester release sheet to a mass per unit area after drying of 80 g/m$^2$, and dried to give a crosslinked gel-like pressure sensitive adhesive layer. The pressure sensitive adhesive layer prepared above was transferred and laminated on an about 400 μm-thick circular knitted fabric having a mass per unit area of 105 g/m$^2$, which was prepared from a polyester fiber having a diameter of about 20 μm and an about circular section, and the laminate was packaged with an aluminum laminate film and aged at 70° C. for 48 hr. Furthermore, the laminate sheet after aging was cut to give an adhesive preparation (length 10 cm, width 14 cm, an edge being a circular arc with a curvature radius of 1 cm).

Example 13

The pressure sensitive adhesive solution containing a drug, which was obtained in the same manner as in Example 1 was. applied onto a 75 μm-thick polyester release sheet to a mass per unit area after drying of 60 g/m$^2$, and dried to give a crosslinked gel-like pressure sensitive adhesive layer. The pressure sensitive adhesive layer prepared above was transferred and laminated on an about 550 μm-thick circular knitted fabric having a mass per unit area of 150 g/m$^2$, which was prepared from a polyester fiber having a diameter of about 20 μm and an about circular section, and the laminate was packaged with an aluminum laminate film and aged at 70° C. for 48 hr. Furthermore, the laminate sheet after aging was cut to give an adhesive preparation (length 10 cm, width 14 cm, an edge being a circular arc with a curvature radius of 1 cm).

Comparative Example 1

To the above-mentioned solution of copolymer A, which has a solid content corresponding to 12 g, were added isopropyl myristate (8 g), glycol salicylate (2 g), trifunctional isocyanate (0.0108 g, CORONATE HL, manufactured by Nippon Polyurethane Industry Co., Ltd.) as a crosslinking agent and a suitable amount of ethyl acetate for adjusting the concentration, and the mixture was stirred to give a homogeneous pressure sensitive adhesive solution containing a drug and having a non-solvent concentration of 30 mass %. The obtained pressure sensitive adhesive solution was applied onto a 75 μm-thick polyester release sheet to a mass per unit area after drying of 60 g/m², and dried to give a crosslinked gel-like pressure sensitive adhesive layer. The pressure sensitive adhesive layer prepared above was transferred and laminated on a 520 μm-thick spunlaced non-woven fabric having a mass of 85 g/m², which was prepared from a polyester crimpy fiber having a diameter of about 20 μm and an about circular section, and the laminate was packaged with an aluminum laminate film and aged at 70° C. for 48 hr. Furthermore, the laminate sheet after aging was cut to give an adhesive preparation (length 10 cm, width 14 cm, an edge being a circular arc with a curvature radius of 1 cm).

Comparative Example 2

To the above-mentioned solution of copolymer A, which has a solid content corresponding to 12 g, were added isopropyl myristate (8 g), glycol salicylate (2 g), trifunctional isocyanate (0.0108 g, CORONATE HL, manufactured by Nippon Polyurethane Industry Co., Ltd.) as a crosslinking agent and a suitable amount of ethyl acetate for adjusting the concentration, and the mixture was stirred to give a homogeneous pressure sensitive adhesive solution containing a drug and having a non-solvent concentration of 30 mass %. The obtained pressure sensitive adhesive solution was applied onto a 75 μm-thick polyester release sheet to a mass per unit area after drying of 60 g/m², and dried to give a crosslinked gel-like pressure sensitive adhesive layer. The pressure sensitive adhesive layer prepared above was transferred and laminated on a 420 μm-thick spunlaced non-woven fabric having a mass per unit area of 100 g/m², which was prepared from a composite fiber made of a polyester fiber (60%) and a polypropylene fiber (40%) having a diameter of about 5-10 μm and an about triangle section, and the laminate was packaged with an aluminum laminate film and aged at 70° C. for 48 hr. Furthermore, the laminate sheet after aging was cut to give an adhesive preparation (length 10 cm, width 14 cm, an edge being a circular arc with a curvature radius of 1 cm).

Comparative Example 3

To the above-mentioned solution of polyisobutylene, which has a solid content corresponding to 16 g, were added isopropyl myristate (3 g), glycol salicylate (1 g), and a suitable amount of a mixture of hexane/tetrahydrofuran (1:1) for adjusting the concentration, and the mixture was stirred to give a homogeneous pressure sensitive adhesive solution containing a drug and having a non-solvent concentration of 20 mass %. The obtained pressure sensitive adhesive solution was applied onto a 75 μm-thick polyester release sheet to a mass per unit area after drying of 60 g/m², and dried to give a crosslinked gel-like pressure sensitive adhesive layer. The pressure sensitive adhesive layer prepared above was transferred and laminated on an about 12 μm-thick polyester single layer film having a mass of 16 g/m², and the laminate was packaged with an aluminum laminate film and aged at 70° C. for 48 hr. Furthermore, the laminate sheet after aging was cut to give an adhesive preparation (length 10 cm, width 14 cm, an edge being a circular arc with a curvature radius of 1 cm).

Comparative Example 4

To the above-mentioned solution of polyisobutylene, which has a solid content corresponding to 16 g, were added isopropyl myristate (3 g), glycol salicylate (1 g), and a suitable amount of a mixture of hexane/tetrahydrofuran (1:1) for adjusting the concentration, and the mixture was stirred to give a homogeneous pressure sensitive adhesive solution containing a drug and having a non-solvent concentration of 20 mass %. The obtained pressure sensitive adhesive solution was applied onto a 75 μm-thick polyester release sheet to a mass per unit area after drying of 60 g/m², and dried to give a crosslinked gel-like pressure sensitive adhesive layer. The pressure sensitive adhesive layer prepared above was transferred and laminated on a nonwoven fabric side of a film obtained by laminating an about 6 μm-thick polyester film (mass 9 g/m²) on a nonwoven fabric (mass 12 g/m²), which was prepared from a polyester fiber having a diameter of about 20 μm and an about circular section, and the laminate was packaged with an aluminum laminate film and aged at 70° C. for 48 hr. Furthermore, the laminate sheet after aging was cut to give an adhesive preparation (length 10 cm, width 14 cm, an edge being a circular arc with a curvature radius of 1 cm).

Comparative Example 5

To the above-mentioned solution of copolymer A, which has a solid content corresponding to 12 g, were added isopropyl myristate (8 g), glycol salicylate (2 g), trifunctional isocyanate (0.0108 g, CORONATE HL, manufactured by Nippon Polyurethane Industry Co., Ltd.) as a crosslinking agent and a suitable amount of ethyl acetate for adjusting the concentration, and the mixture was stirred to give a homogeneous pressure sensitive adhesive solution containing a drug and having a non-solvent concentration of 30 mass %. The obtained pressure sensitive adhesive solution was applied onto a 75 μm-thick polyester release sheet to a mass per unit area after drying of 60 g/m², and dried to give a crosslinked gel-like pressure sensitive adhesive layer. The pressure sensitive adhesive layer prepared above was transferred and laminated on an about 450 μm-thick circular knitted fabric C having a mass per unit area of 110 g/m², which was prepared from a polyester fiber having a diameter of about 20 μm and an about circular section, and the laminate was packaged with an aluminum laminate film and aged at 70° C. for 48 hr. Furthermore, the laminate sheet after aging was cut to give an adhesive preparation (length 10 cm, width 14 cm, an edge being a circular arc with a curvature radius of 1 cm).

Comparative Example 6

Styrene-isoprene-styrene block copolymer (12.5 g, Kraton D-1107CU, manufactured by SHELL KAGAKU KK), polyisobutylene (11.0 g, Oppanol B80, Manufactured by BASF), hydrogenated rosin ester (6.0 g, Steberite ester 7, manufactured by Rika Hercules), liquid paraffin (19.5 g, Crystol J-352, manufactured by Esso Petroleum Co., Ltd.) and propyl gallate (0.5 g) were stirred with heating at 200° C. for 60 min under a nitrogen gas atmosphere to give a pressure sensitive adhesive solution. To this solution was added glycol salicylate at 140° C. (110-180° C.), and the mixture was stirred for 20 min to give a homogeneous pressure sensitive adhesive solution containing a drug. Subsequently, this pressure sensitive adhesive solution was cast on a 75 μm thick polyester release sheet to a mass per unit area of 140 g/m². The pressure sensitive adhesive layer prepared above was transferred and press adhered to an about 450 μm-thick circular knitted fabric C having a mass per unit area of 110 g/m², which was prepared from a polyester fiber having a diameter of about 20 μm and an about circular section. The laminate sheet was cut to give an adhesive preparation (length 10 cm, width 14 cm, an edge being a circular arc with a curvature radius of 1 cm).

Comparative Example 7

Styrene-isoprene-styrene block copolymer (13.0 g, Kraton D-1107CU, manufactured by SHELL KAGAKU KK), polyisobutylene (10.5 g, Oppanol B80, Manufactured by BASF), hydrogenated rosin ester (5.5 g, Ester Gum H, Manufactured by Arakawa Chemical Industries, Ltd.), liquid paraffin (19.0 g, Crystol J-352, manufactured by Esso Petroleum Co., Ltd.), N-methyl-2-pyrrolidone (2.5 g) and propyl gallate (0.5 g) were stirred with heating at 200° C. for 60 min under a nitrogen gas atmosphere to give a pressure sensitive adhesive solution. To this solution was added glycol salicylate at 140° C. (110-180° C.), and the mixture was stirred for 20 min to give a homogeneous pressure sensitive adhesive solution containing a drug. Subsequently, this pressure sensitive adhesive solution was cast on a 75 μm thick polyester release sheet to a mass per unit area of 210 g/m². The pressure sensitive adhesive layer prepared above was transferred and press adhered to an about 450 μm-thick circular knitted fabric C having a mass per unit area of 110 g/m², which was prepared from a polyester fiber having a diameter of about 20 μm and an about circular section. The laminate sheet was cut to give an adhesive preparation (length 10 cm, width 14 cm, an edge being a circular arc with a curvature radius of 1 cm).

Comparative Example 8

Styrene-isoprene-styrene block copolymer (12.5 g, Kraton D-1107CU, manufactured by SHELL KAGAKU KK), polyisobutylene (11.0 g, Oppanol B80, Manufactured by BASF), hydrogenated rosin ester (5.5 g, Steberite ester 7, manufactured by Rika Hercules), liquid paraffin (19.0 g, Crystol J-352, manufactured by Esso Petroleum Co., Ltd.) and propyl gallate (0.5 g) were stirred with heating at 200° C. for 60 min under a nitrogen gas atmosphere to give a pressure sensitive adhesive solution. To this solution was added ketoprbfen (1.5 g) at 140° C. (110-180° C.), and the mixture was stirred for 20 min to give a homogeneous pressure sensitive adhesive solution containing a drug. Subsequently, this pressure sensitive adhesive solution was cast on a 75 μm thick polyester release sheet to a mass per unit area of 140 g/m². The pressure sensitive adhesive layer prepared above was transferred and press adhered to an about 450 μm-thick circular knitted fabric C having a mass per unit area of 110 g/m², which was prepared from a polyester fiber having a diameter of about 20 μm and an about circular section. The laminate sheet was cut to give an adhesive preparation (length 10 cm, width 14 cm, an edge being a circular arc with a curvature radius of 1 cm).

Comparative Example 9

Styrene-isoprene-styrene block copolymer (13.0 g, Kraton D-1107CU, manufactured by SHELL KAGAKU KK), polyisobutylene (10.5 g, Oppanol B80, Manufactured by BASF), hydrogenated rosin ester (5.5 g, Ester Gum H, Manufactured by Arakawa Chemical Industries, Ltd.), liquid paraffin (19.0 g, Crystol J-352, manufactured by Esso Petroleum Co., Ltd.), N-methyl-2-pyrrolidone (2.5 g) and propyl gallate (0.5 g) were stirred with heating at 200° C. for 60 min under a nitrogen gas atmosphere to give a pressure sensitive adhesive solution. To this solution was added diclofenac sodium (1.5 g) at 140° C. (110-180° C.), and the mixture was stirred for 20 min to give a homogeneous pressure sensitive adhesive solution containing a drug. Subsequently, this pressure sensitive adhesive solution was cast on a 75 μm thick polyester release sheet to a mass per unit area of 210 g/m². The pressure sensitive adhesive layer prepared above was transferred and press adhered to an about 450 μm-thick circular knitted fabric C having a mass per unit area of 110 g/m², which was prepared from a polyester fiber having a diameter of about 20 μm and an about circular section. The laminate sheet was cut to give an adhesive preparation (length 10 cm, width 14 cm, an edge being a circular arc with a curvature radius of 1 cm).

Comparative Example 10

To the above-mentioned solution of polyisobutylene, which has a solid content corresponding to 12 g, were added isopropyl myristate (8 g), glycol salicylate (1 g) and a suitable amount of a mixture of hexane/tetrahydrofuran (1:1) for adjusting the concentration, and the mixture was stirred to give a homogeneous pressure sensitive adhesive solution containing a drug and having a non-solvent concentration of 25 mass %. The obtained pressure sensitive adhesive solution was applied onto a 75 μm-thick polyester release sheet to a mass per unit area after drying of 60 g/m², and dried to give a crosslinked gel-like pressure sensitive adhesive layer. The pressure sensitive adhesive layer prepared above was transferred and press adhered on an about 400 μm-thick circular knitted fabric A having a mass per unit area of 105 g/m², which was prepared from a polyester fiber having a diameter of about 20 μm and an about circular section. Furthermore, the laminate sheet was cut to give an adhesive preparation (length 10 cm, width 14 cm, an edge being a circular arc with a curvature radius of 1 cm).

Comparative Example 11

Styrene-isoprene-styrene block copolymer (12.5 g, Kraton D-1107CU, manufactured by SHELL KAGAKU KK), polyisobutylene (11.0 g, Oppanol B80, Manufactured by BASF), hydrogenated rosin ester (6.0 g, Steberite ester 7, manufactured by Rika Hercules), liquid paraffin (19.5 g, Crystol J-352, manufactured by Esso Petroleum Co., Ltd.) and propyl gallate (0.5 g) were stirred with heating at 200° C. for 60 min under a nitrogen gas atmosphere to give a pressure sensitive adhesive solution. To this solution was added diclofenac sodium (1.5 g) at 140° C. (110-180° C.), and the mixture was stirred for 20 min to give a homogeneous pressure sensitive adhesive solution containing a drug. Subsequently, this pressure sensitive adhesive solution was cast on a 75 μm thick polyester release sheet to a mass per unit area of 140 g/m². The pressure sensitive adhesive layer prepared above was transferred and press adhered to an about 400 μm-thick circular knitted fabric A having a mass per unit area of 105 g/m², which was prepared from a polyester fiber having a diameter of about 20 μm and an about circular section. The laminate sheet was cut to give an adhesive preparation (length 10 cm, width 14 cm, an edge being a circular arc with a curvature radius of 1 cm).

Comparative Example 12

Styrene-isoprene-styrene block copolymer (13.0 g, Kraton D-1107CU, manufactured by SHELL KAGAKU KK), polyisobutylene (10.5 g, Oppanol B80, Manufactured by BASF), hydrogenated rosin ester (5.5 g, Ester Gum H, Manufactured by Arakawa Chemical Industries, Ltd.), liquid paraffin (19.0 g, Crystol J-352, manufactured by Esso Petroleum Co., Ltd.), N-methyl-2-pyrrolidone (2.5 g) and propyl gallate (0.5 g) were stirred with heating at 200° C. for 60 min under a nitrogen gas atmosphere to give a pressure sensitive adhesive solution. To this solution was added diclofenac sodium (1.5 g) at 140° C. (110-180° C.), and the mixture was stirred for 20 min to give a homogeneous pressure sensitive adhesive solution containing a drug. Subsequently, this pressure sensitive adhesive solution was cast on a 75 μm thick polyester release sheet to a mass per unit area of 210 g/m². The pressure sensitive adhesive layer prepared above was transferred and press adhered to an about 400 μm-thick circular knitted fabric A having a mass per unit area of 105 g/m², which was prepared from a polyester fiber having a diameter of about 20 μm and an about circular section. The laminate sheet was cut to give an adhesive preparation (length 10 cm, width 14 cm, an edge being a circular arc with a curvature radius of 1 cm).

Comparative Example 13

To the above-mentioned solution of copolymer A, which has a solid content corresponding to 12 g, were added isopropyl myristate (8 g), glycol salicylate (2 g), trifunctional isocyanate (0.0108 g, CORONATE HL, manufactured by Nippon Polyurethane Industry Co., Ltd.) as a crosslinking agent and a suitable amount of ethyl acetate for adjusting the concentration, and the mixture was stirred to give a homogeneous pressure sensitive adhesive solution containing a drug and having a non-solvent concentration of 30 mass %. The obtained pressure sensitive adhesive solution was applied onto a 75 μm-thick polyester release sheet to a mass per unit area after drying of 60 g/m², and dried to give a crosslinked gel-like pressure sensitive adhesive layer. The pressure sensitive adhesive layer prepared above was transferred and laminated on a 400 μm-thick spunlaced non-woven fabric having a mass per unit area of 100 g/m², which was prepared from a composite fiber made of a polyester fiber (60%) and a polypropylene fiber (40%) and having an about triangular section (bottom side 5 μm, height 10 μm), and the laminate was packaged with an aluminum laminate film and aged at 70° C. for 48 hr. Furthermore, the laminate sheet after aging was cut to give an adhesive preparation (length 10 cm, width 14 cm, an edge being a circular arc with a curvature radius of 1 cm).

Comparative Example 14

To the above-mentioned solution of copolymer A, which has a solid content corresponding to 12 g, were added isopropyl myristate (8 g), glycol salicylate (2 g) and a suitable amount of ethyl acetate for adjusting the concentration, and the mixture was stirred to give a homogeneous pressure sensitive adhesive solution containing a drug and having a non-solvent concentration of 30 mass %. The obtained pressure sensitive adhesive solution was applied onto a 75 μm-thick polyester release sheet to a mass per unit area after drying of 60 g/m², and dried to give a crosslinked gel-like pressure sensitive adhesive layer. The pressure sensitive adhesive layer prepared above was transferred and laminated on an about 400 μm-thick circular knitted fabric A having a mass per unit area of 105 gm², which was prepared from a polyester fiber having a diameter of about 20 μm and an about circular section, and the laminate was packaged with an aluminum laminate film and aged at 70° C. for 48 hr. Furthermore, the laminate sheet after aging was cut to give an adhesive preparation (length 10 cm, width 14 cm, the edge being a circular arc with a curvature radius of 1 cm).

The adhesive preparations obtained in Examples 1-5 and Comparative Examples 1-7 were subjected to the following tests. The results of the tests are shown in Table 1.

(1) The mass (CW) per unit area of the support and the mass (AW) per unit area of the pressure sensitive adhesive layer containing a drug were measured according to JIS L 1018: 1990, and CW/AW was calculated.

(2) The static friction coefficient in the shorter size direction of the surface, which is free of a pressure sensitive adhesive layer, of the support was measured according to JIS P 8147: 1994.

(3) The 20% modulus (AM) in the shorter size direction of the adhesive preparation and the 20% modulus (EM) in the longer size direction of the adhesive preparation were measured according to JIS Z 0237:2000 and AM/EM was calculated.

(4) The shear adhesive force in the shorter size direction of the adhesive preparation was measured (N=3) according to JIS Z 0237:1991 and the average value was determined.

TABLE 1

| | mass per unit area (g/m²) | | | static friction coefficient | 20% modulus (N/cm) | | | shear adhesive force |
|---|---|---|---|---|---|---|---|---|
| | CW | AW | CW/AW | (tan θ) | AM | EM | AM/EM | (N/cm²) |
| Ex. 1 | 105 | 60 | 1.7 | 0.69 | 0.9 | 0.8 | 1.1 | 3.0 |
| Ex. 2 | 105 | 60 | 1.7 | 0.68 | 0.9 | 0.8 | 1.1 | 2.8 |
| Ex. 3 | 105 | 60 | 1.7 | 0.69 | 1.0 | 0.9 | 1.1 | 2.0 |
| Ex. 4 | 150 | 60 | 2.5 | 0.66 | 1.2 | 1.2 | 1.0 | 3.6 |
| Ex. 5 | 60 | 40 | 1.5 | 0.38 | 0.6 | 0.5 | 1.2 | 2.5 |
| Com. Ex. 1 | 85 | 60 | 1.4 | 0.82 | 2.1 | 0.6 | 3.5 | 3.7 |
| Com. Ex. 2 | 100 | 60 | 1.7 | 0.83 | 12.6 | 9.0 | 1.4 | 10.1 |
| Com. Ex. 3 | 16 | 60 | 0.3 | 0.21 | measurement not possible | measurement not possible | — | 15.2 |
| Com. Ex. 4 | 21 | 60 | 0.4 | 0.23 | measurement not possible | measurement not possible | — | 14.2 |

TABLE 1-continued

|  | mass per unit area (g/m²) | | | static friction coefficient | 20% modulus (N/cm) | | | shear adhesive force |
|---|---|---|---|---|---|---|---|---|
|  | CW | AW | CW/AW | (tan θ) | AM | EM | AM/EM | (N/cm²) |
| Com. Ex. 5 | 110 | 60 | 1.8 | 0.65 | 1.4 | 0.5 | 2.8 | 3.4 |
| Com. Ex. 6 | 110 | 140 | 0.8 | 0.65 | 1.6 | 0.6 | 2.7 | 4.2 |
| Com. Ex. 7 | 110 | 210 | 0.5 | 0.64 | 1.7 | 0.6 | 2.8 | 2.0 |

Using the adhesive preparations obtained in Examples 1-5 and Comparative Examples 1-7, functional evaluation was performed with 5 volunteers for the adhesion to the skin. To be specific, adhesive preparations cut into the same shape of length 7 cm, width 10 cm (the edge being a circular arc with a curvature radius of 1 cm) were adhered to the chest of the volunteers for 48 hr (shower was allowed, keeping preparation from wetting as far as possible) and (1) foreign body sensation during adhesion, (2) itchiness during adhesion, (3) state during adhesion and (4) glue remainder upon peeling off were evaluated according to the following criteria and the average values were determined. The evaluation results are shown in Table 2.

(1) Foreign Body Sensation During Adhesion

The foreign body sensation during adhesion was graded in six levels of points 0, 1, 2, 3, 4 and 5, based on the functional evaluation of the volunteers, wherein "strikingly felt" is 0 and "not felt at all" is 5.

(2) Itchiness During Adhesion

The itchiness during adhesion was graded in six levels of points 0, 1, 2, 3, 4 and 5, based on the functional evaluation of the volunteers, wherein "strikingly felt" is 0 and "not felt at all" is 5.

(3) State During Adhesion

The state during adhesion was graded 22 hr later, wherein "less than 5% was peeled off" was 5 points, "not less than 5% and less than 10% was peeled off" was 4 points, "not less than 10% and less than 30% was peeled off" was 3 points, "not less than 30% and less than 60% was peeled off" was 2 points, "not less than 60% and less than 100% was peeled off" was 1 point, and "fell off" was 0 point.

(4) Glue Remainder Upon Peeling Off

The glue remainder upon peeling off was graded 22 hr later, wherein "no glue remainder on the periphery" was 5 points, "glue remainder on the periphery was less than 5% of the perimeter" was 4 points, "glue remainder on the periphery was not less than 5% and less than 20% of the perimeter" was 3 points, "glue remainder on the periphery was not less than 20% and less than 50% of the perimeter" was 2 points, "glue remainder on the periphery was not less than 50% and less than 100% of the perimeter" was 1 point, and "glue remainder on all perimeter" was 0 point.

TABLE 2

| | foreign body sensation during adhesion (average value) | itchiness during adhesion (average value) | state during adhesion (average value) | glue remainder upon peeling off (average value) |
|---|---|---|---|---|
| Ex. 1 | 5.0 | 4.8 | 5.0 | 5.0 |
| Ex. 2 | 4.8 | 4.8 | 5.0 | 5.0 |
| Ex. 3 | 4.8 | 4.0 | 4.4 | 5.0 |
| Ex. 4 | 4.8 | 4.6 | 5.0 | 5.0 |
| Ex. 5 | 5.0 | 4.8 | 5.0 | 4.8 |
| Com. Ex. 1 | 3.4 | 4.4 | 3.0 | 4.8 |
| Com. Ex. 2 | 0.8 | 4.0 | 2.2 | 4.8 |
| Com. Ex. 3 | 0.4 | 1.6 | 0.6 | 0.4 |
| Com. Ex. 4 | 0.6 | 2.6 | 0.8 | 0.6 |
| Com. Ex. 5 | 2.8 | 4.0 | 4.0 | 4.4 |
| Com. Ex. 6 | 2.4 | 2.6 | 4.2 | 4.8 |
| Com. Ex. 7 | 2.0 | 1.8 | 4.4 | 4.8 |

The adhesive preparations obtained in Examples 1, 8-13 and Comparative Examples 10-14 were wrapped with an aluminum laminate film, preserved at 25° C. under 60% relative humidity for 3 months and subjected to the following tests. The test results are shown in Table 3.

(1) The amount of moisture permeation was measured according to JIS L 1099:1993.

(2) The amount of moisture permeation inherent to the cloth used in Examples 1, 8-13 and Comparative Examples 10-12, 14 was taken as 11420 g/m²·24 hr, and the amount of moisture permeation inherent to the cloth used in Comparative Example 13 was taken as 9700 g/m²·24 hr, the amount of moisture permeation remaining after production of the adhesive preparations was calculated.

(3) The 20% modulus in one direction was measured according to JIS Z 0237:2000.

(4) The adhesion to a bakelite plate was measured according to JIS Z 0237:2000.

(5) The shear adhesive force was measured (N=3) according to JIS Z 0237:2000, and the average value was determined.

TABLE 3

| | amount of moisture permeation (g/m² · 24 hr) | ratio (%) of remaining amount of moisture permeation | 20% modulus (N/cm) | adhesion to bakelite plate (N/24 mm width) | shear adhesive force (N/cm²) |
|---|---|---|---|---|---|
| Ex. 1 | 1250 | 11 | same as in Table 1 | 0.48 | 3.0 |
| Ex. 8 | 1300 | 11 | 0.83 | 0.43 | 2.8 |
| Ex. 9 | 1470 | 13 | 0.77 | 0.51 | 3.3 |
| Ex. 10 | 1880 | 16 | 0.72 | 0.29 | 2.2 |
| Ex. 11 | 1520 | 13 | 0.73 | 0.37 | 2.4 |
| Ex. 12 | 990 | 9 | 0.84 | 0.55 | 3.7 |
| Ex. 13 | 1110 | 10 | 1.22 | 0.50 | 3.2 |
| Com. Ex. 10 | not measured | — | 0.85 | measurement not possible | measurement not possible |
| Com. Ex. 11 | 220 | 2 | 1.15 | 0.96 | 4.2 |
| Com. Ex. 12 | 120 | 1 | 0.88 | 0.29 | 2.0 |
| Com. Ex. 13 | 1020 | 11 | 7.76 | 0.69 | 10.0 |
| Com. Ex. 14 | not measured | — | 0.83 | measurement not possible | measurement not possible |

In Table 3, "measurement not possible" means that the measurement was unattainable because the pressure sensitive adhesive layer sank in cloth leaving no pressure sensitive adhesive on the surface, which resulted into the disappearance of adhesiveness.

Using the adhesive preparations obtained in Examples 1, 9, 13 and Comparative Examples 11-13, functional evaluation was performed with 5 volunteers for the adhesion to the skin after preservation for 3 months. To be specific, adhesive preparations cut into the same shape of length 7 cm, width 10 cm (the edge being a circular arc with a curvature radius of 1 cm) were adhered to the chest of the volunteers for 72 hr (shower was allowed, keeping preparation from wetting as far as possible) and (1) foreign body sensation during adhesion, (2) itchiness during adhesion, (3) fell off or not and (4) pain upon peeling off were evaluated according to the following criteria and the average values were determined. The evaluation results are shown in Table 4.

(1) Foreign Body Sensation During Adhesion

The foreign body sensation during adhesion was graded in six levels of points 0, 1, 2, 3, 4 and 5, based on the functional evaluation of the volunteers, wherein "strikingly felt" is 0 and "not felt at all" is 5.

(2) Itchiness During Adhesion

The itchiness during adhesion was graded in six levels of points 0, 1, 2, 3, 4 and 5, based on the functional evaluation of the volunteers, wherein "strikingly felt" is 0 and "not felt at all" is 5.

(3) Fell Off or Not

Whether the preparation fell off or not was graded wherein "the preparation did not fall off for 72 hr after adhesion" was 5 points, "the preparation did not fall off for 48 hr after adhesion" was 4 points, "the preparation did not fall off for 24 hr after adhesion" was 3 points, "the preparation did not fall off for 12 hr after adhesion" was 2 points, "the preparation did not fall off for 6 hr after adhesion" was 1 point, and "the preparation fell off within 6 hr after adhesion" was 0 point.

(4) Pain Upon Peeling Off

The pain upon peeling off was graded in six levels of points 0, 1, 2, 3, 4 and 5, based on the functional evaluation of the volunteers, wherein "strikingly felt" is 0 and "not felt at all" is 5. When the preparation fell off within 72 hr after adhesion, the preparation was removed from the evaluation object.

TABLE 4

| | foreign body sensation during adhesion (average value) | itchiness during adhesion (average value) | fell off or not (average value) | pain upon peeling off (average value) |
|---|---|---|---|---|
| Ex. 1 | 4.8 | 4.8 | 5.0 | 4.8 |
| Ex. 9 | 4.6 | 4.8 | 5.0 | 4.6 |
| Ex. 13 | 4.8 | 4.6 | 5.0 | 4.6 |
| Com. Ex. 11 | 4.0 | 2.2 | 3.4 | 1.0 (preparation fell off in one volunteer) |
| Com. Ex. 12 | 3.6 | 1.8 | 3.3 | 1.5 (preparation fell off in one volunteer) |
| Com. Ex. 13 | 0.8 | 4.4 | 4.6 | 3.0 |

From the above results, it has been confirmed that the adhesive preparations of Examples 1-13 are superior in comfortable feeling of adhesion because they hardly accompany foreign body sensation and itchiness during adhesion, and glue remainder during adhesion and peeling off seldom occur because friction of the support is small. Moreover, the adhesive preparations do not get peeled off or fall off during putting on/taking off of clothes and during adhesion. Furthermore, it has been confirmed that they do not fall off even after 3 days of adhesion, and can be applied for a long time.

This application is based on a patent application No. 2005-116081 filed in Japan, the contents of which are hereby incorporated by reference.

What is claimed is:

1. An adhesive preparation comprising a support made of a cloth, wherein said cloth is a knitted fabric made of a synthetic fiber, and a pressure sensitive adhesive layer formed on one surface of the support, which comprises a pressure sensitive adhesive and a drug, wherein said pressure sensitive adhesive layer is directly laminated on said cloth, wherein said pressure sensitive adhesive comprises an acrylic copolymer obtained by copolymerization of a monomer mixture comprising (meth)acrylic acid alkyl ester as a main component, wherein said acrylic copolymer is crosslinked with a crosslinking agent, and wherein a mass (CW) per unit area of said support is 60-160 g/m², a ratio (CW/AW) of a mass (CW) per unit area of the above-mentioned support and a mass (AW) per unit area of the above-mentioned pressure sensitive adhesive layer is 1.0-5.0, an adhesive layer-free surface of said support has a static friction coefficient of 0.25-0.75, and a 20% modulus (AM) in one direction of the adhesive preparation and a 20% modulus (EM) in the direction perpendicular to said direction are each 0.5-1.5 N/cm, and the ratio thereof (AM/EM) is 0.5-2.0.

2. The adhesive preparation of claim 1, which has a shear adhesive force of 1.0-7.0 N/cm².

3. The adhesive preparation of claim 1, wherein said cloth is made of polyethylene terephthalate.

* * * * *